US00PP15088P3

(12) United States Plant Patent
Zaiger et al.

(10) Patent No.: US PP15,088 P2
(45) Date of Patent: Aug. 17, 2004

(54) INTERSPECIFIC TREE NAMED: MARCIA'S FLAVOR

(50) Latin Name: *Prunus salicina*
Varietal Denomination: Marcia's Flavor

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 42 days.

(21) Appl. No.: 10/327,175

(22) Filed: Dec. 23, 2002

(65) Prior Publication Data

US 2004/0123355 P1 Jun. 24, 2004

(51) Int. Cl.[7] ..... A01H 5/00
(52) U.S. Cl. ..... Plt./180
(58) Field of Search ..... Plt./180

*Primary Examiner*—Anne Marie Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth with heavy and regular production of fruit.
2. Fruit with excellent flavor and eating quality.
3. Fruit with an attractive red skin color.
4. Fruit with high Brix (soluble solids) average of 19.2°.
5. Maturity of fruit being relatively uniform throughout the tree.
6. Firm fruit with good storage and shipping quality.

1 Drawing Sheet

Latin name of the genus and species: Botanical classification: [(*Prunus salicina*×(*Prunus salicina*×*Prunus armeniaca*)×(*Prunus salicina*×*Prunus armeniaca*))]×[((*Prunus salicina*×*Prunus armeniaca*)×(*Prunus salicina*))×(*Prunus salicina*)].

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plums and interspecific trees, which are known to us, and mentioned herein, 'Flavor Gem' Interspecific (U.S. Plant Pat. No. 10,915), 'Royal Zee' Plum (U.S. Plant Pat. No. 5,486) and 'Red Beaut' Plum (U.S. Plant Pat. No. 2,539).

STATEMENT REGARDING FEDERALLY SPONSORED RESEARCH AND DEVELOPMENT

Not applicable.

ORIGIN OF THE VARIETY

The present new variety of interspecific tree [((Plum× Plumcot)×Plumcot)×[((Plumcot×Plum)×Plum)] was developed by us in our experimental orchard located near Modesto, Calif., as a first generation cross of a proprietary parent with the field identification number 16GG159 with 'Flavor Gem' Interspecific (U.S. Plant Pat. No. 10,915). The maternal parent (16GG159) originated from crosses of proprietary selections of plums (*Prunus salicina*) with plumcots (*Prunus salicina*×*Prunus armeniaca*), which were seedling selections that were used in our breeding program. We planted and grew a large number of these first generation seedlings on their own root system, under close and careful observation, during which time one such seedling, which is the present variety, exhibited desirable tree and fruit characteristics and was selected in 1993 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree is of large size, vigorous, upright growth and a heavy and regular bearer of large size, clingstone fruit with a mild, sweet flavor and excellent eating quality. The fruit is further characterized by having an attractive red skin color, being nearly uniform in size throughout the tree, nearly globose in shape with even ripening and high soluble solids (Brix 19.2°). In comparison to the fruit of the interspecific tree 'Flavor Gem'

(U.S. Plant Pat. No. 10,915), the new variety is clingstone instead of freestone and is approximately 20 days earlier in maturity. In comparison to the 'Royal Zee' Plum (U.S. Plant Pat. No. 5,486), the new fruit is approximately 35 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Pruned to 3 to 3.5 meters in height for economical harvesting of fruit.

*Vigor.*—Vigorous. Tree growth of 1.5 to 2 meters in first growing season.

*Form.*—Upright, usually pruned to vase shape.

*Branching habit.*—Upright, crotch angle approximately 30°.

*Productivity.*—Productive. Thinning and spacing of fruit necessary.

*Bearer.*—Regular. Adequate fruit set 3 consecutive years, no alternate bearing observed.

*Fertility.*—Self-sterile, pollenizer required.

*Density.*—Medium dense. Usually pruned to vase shape to allow sunlight to center of tree to improve fruit color and health of fruit spurs.

*Hardiness.*—Hardy in all stone fruit growing areas of California. Winter chilling requirement approximately 650 hours at or below 45° F.

Trunk:

*Size.*—Large, stocky. Average circumference 40.6 cm at 20.3 cm above ground on a 6 year old tree.

*Stocky.*—Medium.

*Texture.*—Medium shaggy, increases with age of tree.

*Color.*—Varies from 10YR 5/2 to 5YR 5/2.

Branches:

*Size.*—Medium. Average circumference 13.4 cm, measured at 86.8 cm above ground. Crotch angle approximately 30°, increases with heavy fruit production.

*Surface texture.*—New growth smooth, more mature growth medium rough.

*Lenticels.*—Average number of 24 in 25.8 square cm surface. Average length 3.7 mm. Average width 1.6 mm. Color 2.5YR 6/8.

*Color.*—New growth varies from 2.5GY 6/6 to 5YR 6/6, where exposed to direct sunlight. Mature growth varies from 7.5YR 4/4 to 7.5YR 3/6. Darkens with age of growth.

Leaves:

*Size.*—Large. Average length 112.8 mm. Average width 42 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slightly indented over veins and midrib, glabrous. Lower surface relatively smooth, small ridges created by midrib and pinnate venation, glabrous.

*Petiole.*—Long, slender. Average length 18.4 mm. Average width 1.6 mm. Longitudinally grooved, glabrous. Color 7.5GY 8/8.

*Glands.*—Globose. Small. Average length 0.9 mm. Average diameter 0.6 mm. Number varies from 1 to 4, average 3. Located on base of leaf blade and upper portion of petiole. Color — 7.5GY 8/6.

*Color.*—Upper surface 7.5GY 4/4. Lower surface 7.5GY 6/4. Midvein color 5GY 8/4.

Flower buds:

*Size.*—Medium. Average length 7.8 mm. Average diameter 4.8 mm. Varies with degree of maturity.

*Hardiness.*—Hardy with respect to California winter climates in stone fruit growing areas.

*Form.*—Conical, becoming elongated before opening.

*Pedicel.*—Average length 13.9 mm. Average width 2.0 mm. Color 2.5GY 7/8.

*Color.*—N 9.5/.

*Number of buds per spur.*—Varies from 13 to 21, average 17.

Flowers:

*Size.*—Medium. Average height 10.2 mm. Average diameter 20.3 mm.

*Petals.*—Number 5, alternately arranged to sepals. Shape — ovate, narrow at point of attachment. Average height 7.2 mm. Average width 6.5 mm. Color N 9.5/. Margin — entire.

*Sepals.*—Number 5, alternately arranged to petals. Shape — ovate, apex rounded. Both surfaces glabrous. Average length 2.6 mm. Average width 2.2 mm. Color — upper surface 5GY 8/6. Lower surface 5GY 7/4.

*Stamens.*—Average number per flower 32. Average filament length 9.0 mm. Filament color N 9.5/. Anther color 2.5Y 8/10.

*Pollen.*—Self-sterile, pollenizer required. Color 2.5Y 8/8.

*Pistil.*—Number — usually 1, varies from 1 to 2. Average length 8.8 mm. Surface — glabrous. Average height of stigma compared to anthers is 1.1 mm lower. Color 2.5GY 9/4.

*Fragrance.*—Slight aroma.

*Blooming period.*—Date of First Bloom Feb. 15, 2001. Date of Petal Fall Feb. 26, 2001. Varies slightly with climatic conditions.

*Color.*—N 9.5/.

*Number flowers per flower bud.*—Usually 2, varies from 1 to 3.

*Pedicel.*—Medium size, glabrous. Average length 14.2 mm. Average width 2.1 mm. Color 2.5GY 7/8.

Fruit:

*Maturity when described.*—Firm ripe.

*Date of first picking.*—Jul. 23, 2001.

*Date of last picking.*—Jul. 29, 2001. Varies slightly with climatic conditions.

*Size.*—Large. Average diameter axially 60.7 mm. Average transversely in suture plane 62.1 mm. Average weight 176.1 grams, varies slightly with fertility of the soil, amount of thinning and climatic conditions.
*Form.*—Globose.
*Suture.*—Nearly smooth, extends from base to apex.
*Ventral surface.*—Slightly lipped.
*Apex.*—Varies from rounded to slightly retuse.
*Base.*—Retuse.
*Cavity.*—Rounded to slightly elongated in suture plane. Average depth 3.2 mm. Average diameter 6.2 mm.

Stem:
*Size.*—Medium. Average length 16.5 mm. Average diameter 2.6 mm.
*Color.*—Varies from 2.5GY 7/4 to 2.5GY 7/6. Varies slightly with exposure to direct sunlight.

Flesh:
*Ripens.*—Evenly.
*Texture.*—Firm, meaty.
*Fibers.*—Few, small, tender.
*Firmness.*—Good, comparable to 'Red Beaut' Plum (U.S. Plant Pat. No. 2,539).
*Aroma.*—Slight.
*Amydgalin.*—Undetected.
*Eating quality.*—Excellent.
*Flavor.*—Excellent, sweet, mild, good balance between acid and sugar.
*Juice.*—Moderate, enhances flavor.
*Brix.*—Average 19.2°, varies slightly with amount of fruit per tree and climatic conditions.
*Color.*—Varies from 5Y 8.5/6 to 2.5Y 5/10, with slight bleeding of color near skin surface. Pit cavity varies from 2.5YR 6/6 to 2.5YR 6/8.

Skin:
*Thickness.*—Medium.
*Surface.*—Smooth.
*Bloom.*—Moderate, complete coverage.
*Tendency to crack.*—Slight, increases with wet weather conditions.
*Color.*—Ground color varies from 5Y 8/6 to 5Y 8.5/6. Overspread with 5R 2/8 to 5R 3/6. Very small, randomly spaced areas of exposed ground color giving a speckling pattern to surface.
*Tenacity.*—Tenacious to the flesh.
*Astringency.*—Undetected.

Stone:
*Type.*—Clingstone.
*Size.*—Large. Average length 28.3 mm. Average width 22.0 mm. Average thickness 11.9 mm.
*Form.*—Obovate.
*Base.*—Varies from straight to slightly retuse.
*Apex.*—Acuminate. Average length 2.3 mm.
*Surface.*—Varies from smooth to lightly pitted. One long groove on each side of suture plane creating a narrow ridge running from base to apex. Several small, short ridges starting from base extending toward apex.
*Sides.*—Unequal, one side extending further outward on suture side of stone.
*Ridges.*—Small, narrow, relatively smooth.
*Tendency to split.*—None.
*Color.*—Varies from 2.5Y 8.5/6 to 2.5Y 8/6 when dry.

Kernal:
*Form.*—Ovate.
*Taste.*—Bitter.
*Viability.*—Viable, embryo developed.
*Size.*—Medium to large. Average length 17.1 mm. Average width 11.5 mm. Average thickness 5.1 mm.
*Skin color.*— 10YR 7/8.

Use: Dessert. Market — local and long distance.

Keeping quality: Good, held firm in cold storage 21 days at 38° to 42° F. without shriveling, internal flesh breakdown or appreciable loss of flavor.

Shipping quality: Good, minimal skin scarring or flesh bruising during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, substantially as illustrated and described, characterized by its large size, vigorous upright growth and being a productive and regular bearer of large size, yellow flesh, clingstone fruit with excellent flavor and eating quality; the fruit is further characterized by having good storage and shipping quality and, in comparison to the 'Flavor Gem' Interspecific (U.S. Plant Pat. No. 10,915) the fruit is clingstone instead of freestone and is approximately 20 days earlier in maturity.

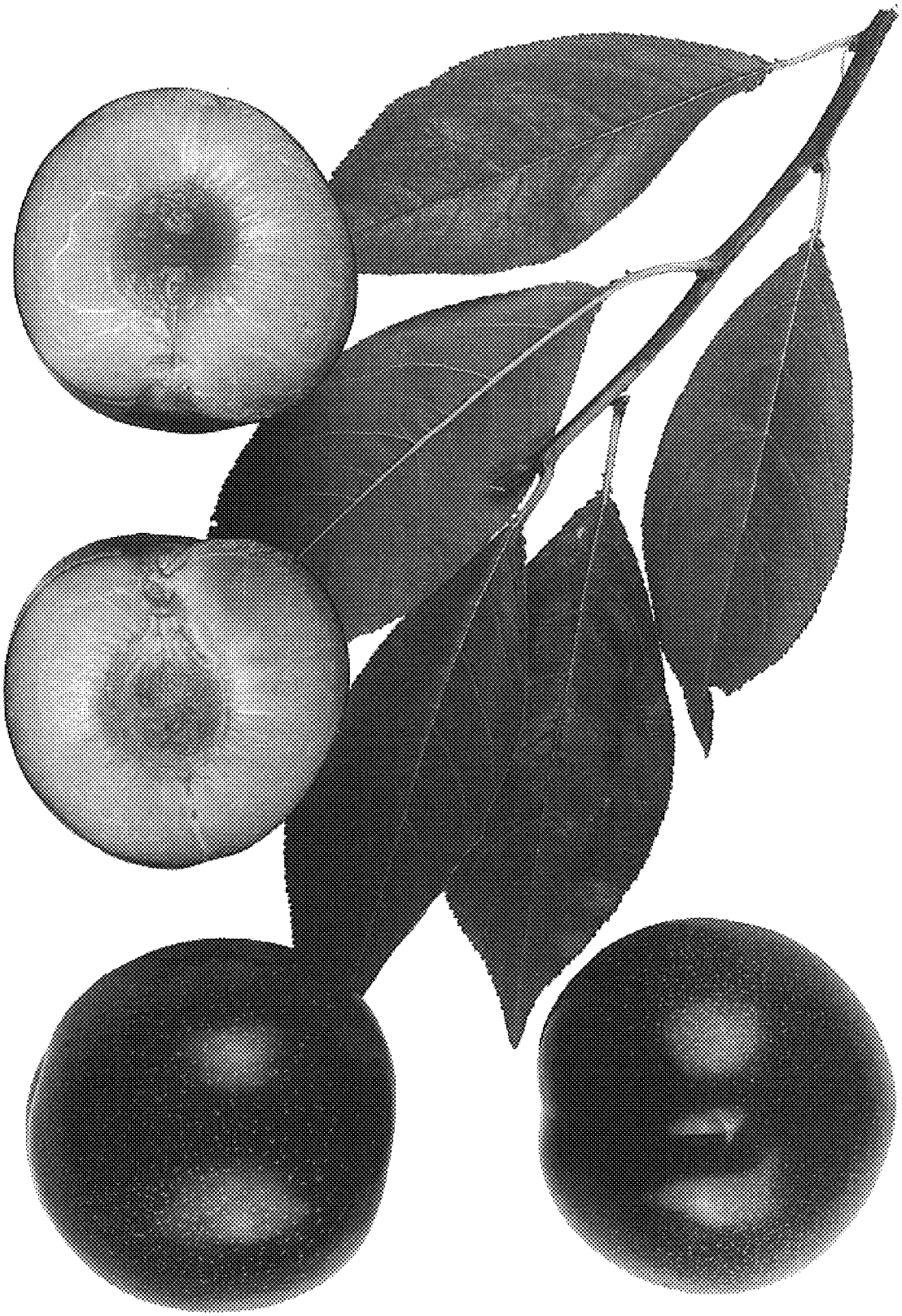

* * * * *